United States Patent
Huntley

(10) Patent No.: US 6,932,978 B2
(45) Date of Patent: Aug. 23, 2005

(54) DOUBLE-HEADED, CLOSED-MOUTH COUGH SUPPRESSANT AND COLD RELIEF DEVICE

(76) Inventor: James Benjamin Huntley, 3636 16th St., NW. #A564, Washington, DC (US) 20010

( * ) Notice: Subject to any disclaimer, the term of this patent is extended or adjusted under 35 U.S.C. 154(b) by 2 days.

(21) Appl. No.: 09/978,790

(22) Filed: Oct. 18, 2001

(65) Prior Publication Data
US 2003/0077319 A1 Apr. 24, 2003

(51) Int. Cl.[7] .......................... A61K 47/00; A61F 13/00; A01N 59/00
(52) U.S. Cl. .................. 424/439; 424/422; 424/435; 424/725; 424/742; 424/747; 424/440; 514/849
(58) Field of Search ...................... 424/400, 422, 424/434, 439, 440, 484, 435, 725, 742, 747; 814/849

(56) References Cited

U.S. PATENT DOCUMENTS

| | | | | |
|---|---|---|---|---|
| 4,671,953 A | * | 6/1987 | Stanley et al. | 424/440 |
| 4,902,519 A | * | 2/1990 | Ream et al. | 426/91 |
| 4,929,446 A | * | 5/1990 | Bartolucci | 424/439 |
| 4,981,394 A | | 1/1991 | McLaren et al. | 405/129 |
| 5,039,529 A | | 8/1991 | Bergendal et al. | 424/630 |
| 5,073,374 A | | 12/1991 | McCarty | 424/435 |
| 5,176,151 A | * | 1/1993 | Harding | 128/842 |
| 5,240,694 A | * | 8/1993 | Gwaltney, Jr. | 424/45 |
| 5,615,941 A | * | 4/1997 | Shecter | 362/109 |
| 5,702,742 A | * | 12/1997 | Jones | 426/115 |
| 5,762,946 A | | 6/1998 | Gueret | 424/401 |
| 5,785,988 A | | 7/1998 | Fust | 424/435 |
| 5,785,989 A | * | 7/1998 | Stanley et al. | 424/440 |
| 5,938,153 A | * | 8/1999 | Coleman et al. | 248/160 |
| 6,623,767 B1 | * | 9/2003 | Morice | 424/745 |

* cited by examiner

*Primary Examiner*—Gary Kunz
(74) *Attorney, Agent, or Firm*—Arent Fox

(57) ABSTRACT

A double-headed, closed-mouth cough suppressant and cold relief device in which an individual having the symptoms of a cough is able to suppress the cough by inserting the device into an open mouth, and by sucking on one end of the device, is able to release a menthol medicament disposed within the device to thereby suppress a cough. Additionally, by sucking on another end of the device a eucalyptus medicament is released to thereby relieve a sore throat. By suppressing the cough, the device prevents the spread of germs to the immediate environment.

14 Claims, 4 Drawing Sheets

DOUBLE-HEADED, CLOSED-MOUTH COUGH SUPPRESSANT AND COLD RELIEF DEVICE

BACKGROUND

Coughing is the body's way of getting foreign substances, phlegm and mucus out of the respiratory tract. Coughs are generally useful and preferably not eliminated. However, in many instances, coughs can be severe enough to impair breathing or prevent rest. Water and other liquids, such as fruit juice, have been traditionally used to soothe an irritated throat as a result of severe coughing. Liquids also moisten and thin the mucus in the throat so that it can be coughed up and expelled more easily. The cough suppressant controls or suppresses an irritating or nagging cough as it subdues the body's coughing reflex.

RELATED ART

Cough suppressants of the prior art include freestanding lozenges that can be removed from a wrapper and placed in the mouth. However, when a cough arises during the course of releasing the substance from the lozenge, the mouth naturally opens. As a result, the lozenge may be abruptly expelled from the mouth during a cough. In addition, germs are also released from the mouth during the resulting open-mouthed cough. Thus, current cough suppressants have the disadvantage of not preventing the spread of germs, and the tendency to be abruptly released from the mouth, and thereby becoming unsanitary and no longer usable.

Liquid cough suppressants are contained within a bottle and contain a medicament in a fluid. The liquid is dispensed by means of cups or spoons. The bottle generally is available with a cap and a small cup into which a small dosage of the liquid is poured. After use, the bottle must be capped and the cup must be cleaned and placed back on the cap in an inverted position. As a result of the dispensable liquid cough suppressant of the prior art, it is generally difficult to make use of the bottle and liquid cough suppressant in an urgent situation, because a number of steps must be performed before and after the use of the liquid cough suppressant. It is also difficult to make use of the bottled liquid cough suppressant in a public venue as the user must be able to clean the cup, or risk the remaining fluid in the cup running down the side of the bottle when placed back in the designated location. Furthermore, those bottles that do not come with cups require spoons to dispense the medicament, also leading to an unsanitary and messy situation when used away from sanitizing facilities. Moreover, the liquid medicaments are prone to accidental spilling.

Today's cough suppressants and cold relief medications do not provide the double-headed medicament, wherein two different medications are disposed at opposite ends of an elongate member. Thus, a cough and cold sufferer is required to carry two different forms of medicine to suppress a cough and sooth a throat to achieve the same benefit as the present invention.

The present invention solves the above-mentioned problems in the prior art and provides a convenient way to dispense a cough suppressant and cold relief device that is sanitary, easy to administer, convenient, readily useable, and cost efficient.

SUMMARY OF THE INVENTION

The generally available cough suppressants, such as lozenges are of the closed-mouthed type, such that when a cough arises in a user the lozenge, although disposed within the mouth, allows the user to cough with their mouth open. However, the Applicant of the present invention as found that a method of controlled breathing while using the device of the present invention, can suppress the cough. In view of this discovery, the Applicant of the present invention has devised an apparatus and method of suppressing a cough and soothing soothes the throat of the user, as well as reducing the wholesale spread of germs, common with the use of prior art cough suppressant devices and which result from an open-mouthed cough. By suppressing the open-mouthed cough, fewer germs are spread, reducing the spread of colds. As a result, fewer people would become sick thereby reducing lost work time. Therefore, the device of the present invention can reduce health-related costs.

In a first embodiment of the present invention, a closed-mouth cough suppressant and cold relief device has a rigid elongate member with opposite ends and an oral medicament disposed at each of the opposite ends. The oral medicament comprises a menthol oral medicament and a eucalyptus oral medicament. The menthol medicament suppresses a cough and the eucalyptus medicament soothes the user's throat. The oral medicaments each have an aperture disposed therein and one of the opposite ends of the elongate member is disposed within the apertures of the oral medicament.

In a second embodiment, a pair of elongate member portions having at least one oral medicament at each end thereof is operatively connected to each other at their opposite ends in a male/female arrangement. The elongate member portions are readily detachable from each other by pulling the elongate member portions in opposite directions, thereby allowing each elongate member portion and respective oral medicament to be separated.

In a third embodiment, a pair of elongate member portions having at least one oral medicament disposed at the end of each elongate member, is parallel to each other. An adhesive joins the lateral sides of the parallel elongate member portions.

An object of the invention is to provide a closed mouthed cough suppressant device that provides an oral medicament in a convenient, easy to administer and sanitary manner.

A second object of the invention is to provide a holding mechanism for a cough suppressant such that during a coughing episode, the user will have a retentive incentive to keep their mouth closed. As a result of the closed-mouthed cough, fewer germs are released from the user's mouth leading to a reduced incidence of colds spreading and a corresponding reduction in health related costs can be achieved.

A third object of the invention is to provide a detachably releasable pair of elongate member portions that are connected at their opposite ends such that the user can selectively engage the medicament of a first portion of the cough suppressant device and retain a second portion of the device for later application or use.

A fourth object of the invention is to provide a method for suppressing a cough.

A fifth object of the invention is to provide a medicament for soothing a throat after coughing.

DETAILED DESCRIPTION OF THE PREFERRED EMBODIMENT

Figure 1:
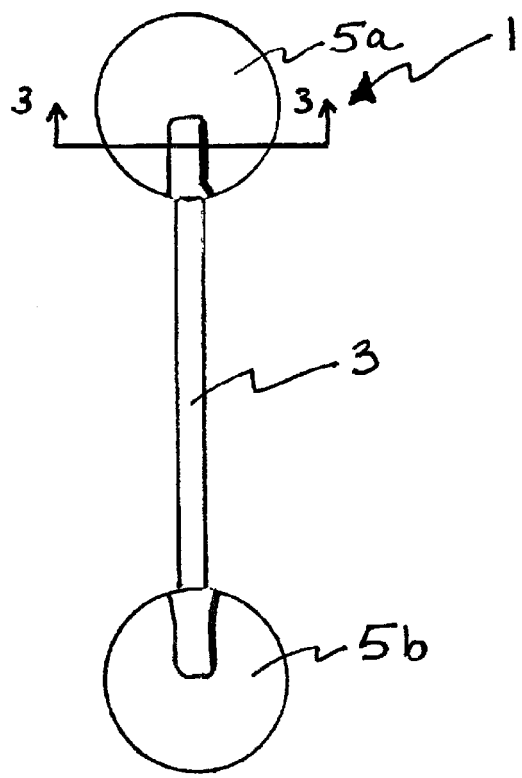
FIG. 1 is a top plan view of the present invention.
Figure 2:
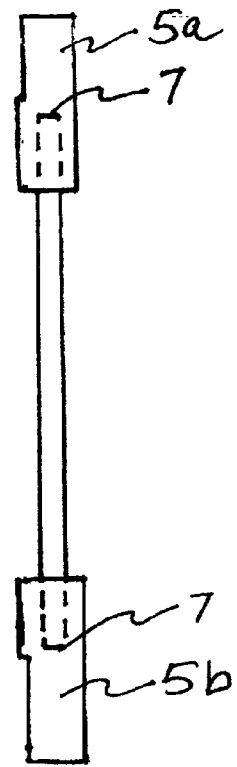
FIG. 2 is a side view of the present invention.
Figure 3:
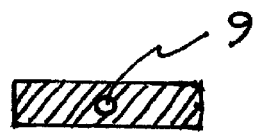
FIG. 3 is a view of the present invention along lines 3—3 of FIG. 1.

FIGS. 1–3 illustrate the first embodiment of the double-headed closed-mouth cough suppressant and cold relief device 1 in accordance with the present invention. The device 1 includes an elongate member 3 having opposite ends 7 and oral medicaments 5a, 5b disposed at opposite ends 7 of the elongate member 3. Each end 7 of the elongate member 3 is embedded within an aperture 9 of the oral medicaments. The oral medicaments illustrated are circular, but may be any other shape having a curved perimeter. The curved perimeter prevents the user from being cut by a sharp edge of the medicament. The apertures 9 in the oral medicaments 5a, 5b are made such that the elongate member 3 can be securely fixed within the oral medicaments. The elongate member 3 is rigid so that it can sustain the weight of the oral medicaments 5a, 5b at each end 7. The elongate member 3 can be fabricated from any number of materials such as paper or plastic.

The oral medicaments 5a, 5b of the present invention are cough suppressants such as menthol and cold symptom relievers such as eucalyptus, which soothes the throat after the user has coughed. The oral medicaments 5a, 5b suppress an impending cough by releasing the medicament into the throat when the user sucks on the medicament 3. The active ingredients in the medicaments can come from any other kind of natural vegetation or manufactured solution either chemical, biological or the like for suppressing a cough. The oral medicaments are solid members that dissolve upon contact with fluid.

The oral medicaments 5a, 5b can have a flavor such as, for examples only, cherry, orange, banana, grape or pineapple.

Figure 4:
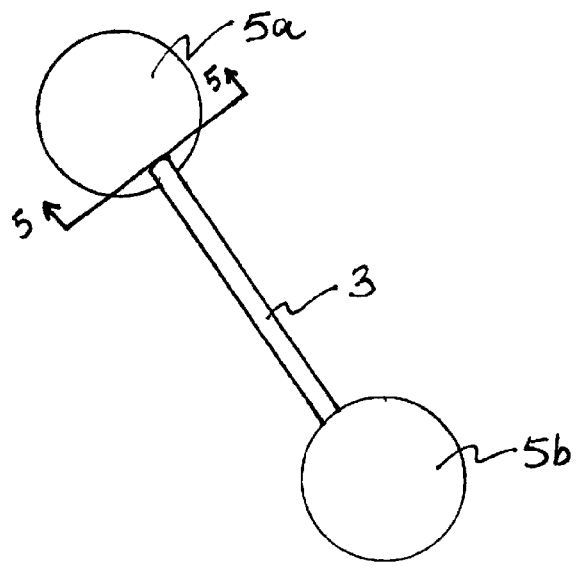
FIG. 4 is a perspective view of a second embodiment of the present invention
Figure 5:
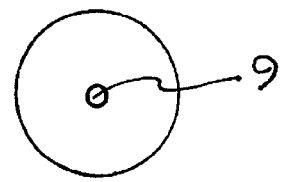
FIG. 5 is a view of the second embodiment of the present invention along lines 5—5 of FIG. 4.

Another embodiment of the closed mouth cough suppressant and cold relief device is illustrated in FIGS. 4 and 5. These Figures illustrate oral medicaments 5a, 5b that are spherical in shape. The spherical shape of the oral medicaments 5a, 5b provides a natural contour to the inside of the user's mouth.

Figure 8:
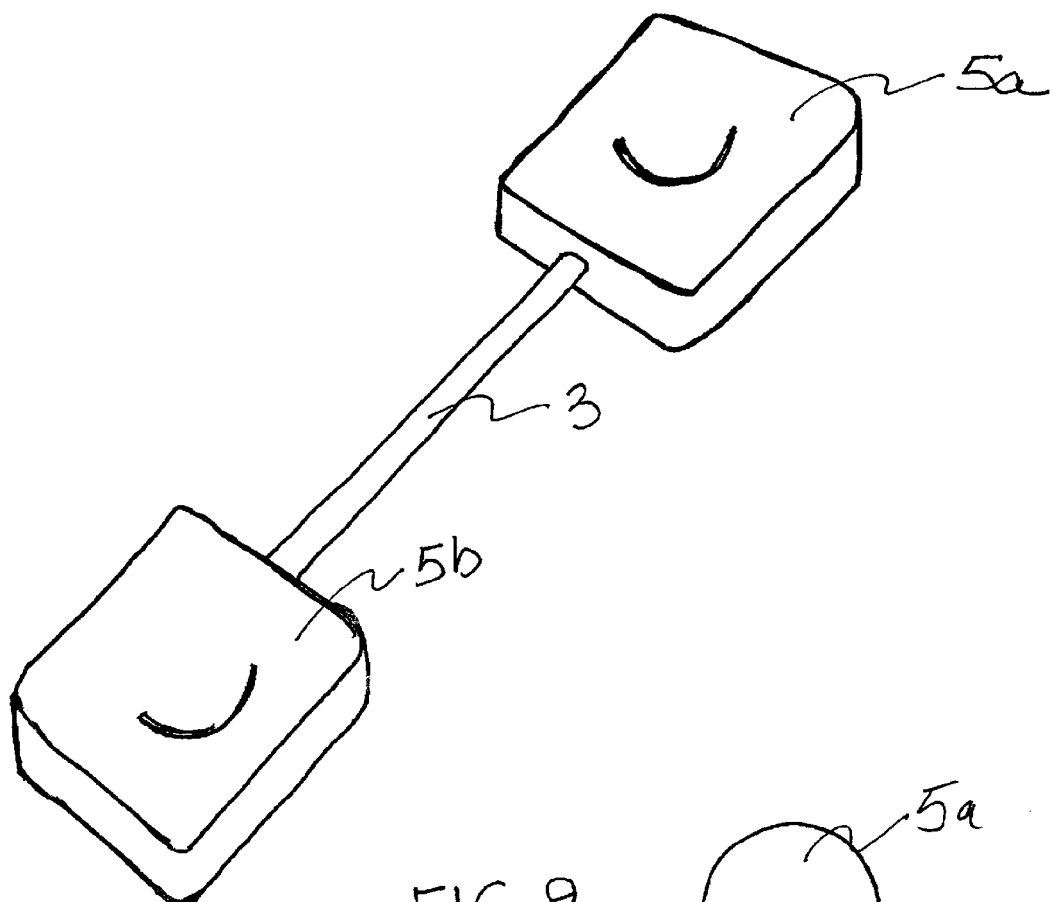
FIG. 8 is a perspective view of a fourth embodiment of the present invention.

In general, the oral medicaments 5a, 5b can be in the form of lozenge as shown in FIG. 8, or a sphere, a disk or any shape that has curved edges. It is preferable that the oral medicaments 5a, 5b have curved edges all around so that the user's mouth is not cut by sharp edges.

Figure 6:
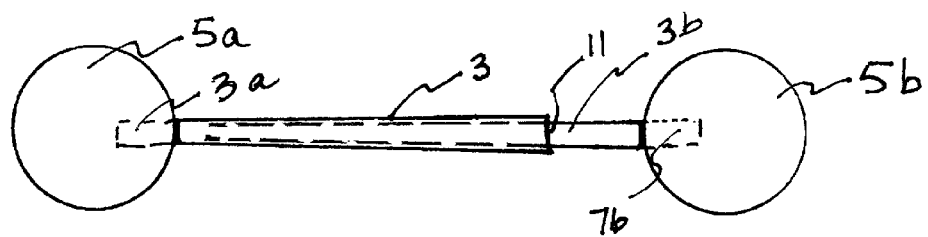
FIG. 6 is a view of a male/female arrangement of the elongate member portions of the present invention.

The elongate member 3 of the device can also be comprised of two individual elongate member portions 3a, 3b. Specifically, the device can be joined and separated in a male/female arrangement so that the user has the option of using the menthol medicament initially, while saving the eucalyptus medicament for later. A first elongate member portion 3b as shown in FIG. 6 has a tapered end and an oral medicament disposed at an end opposite to the tapered end. The second elongate member portion 3a is hollow and larger in diameter that the first elongate member portion 3b. The second elongate member portion 3a has a tapered first end on which one of the oral medicaments is disposed. The tapered end of the first elongate member portion 3b is insertable into the second elongate member portion 3a through the hollow opening 11 of the second elongate member portion 3a in a male/female manner. The first and second elongate member portions 3a, 3b are readily separated by being pulled in opposite directions.

Figure 9:
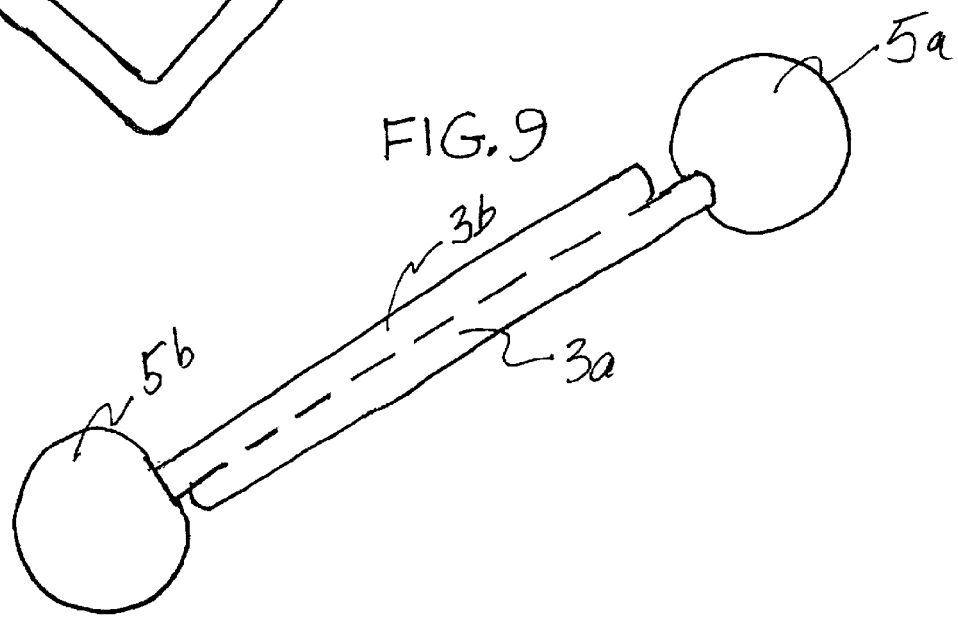
FIG. 9 is a perspective view of a fifth embodiment of the present invention.

As shown in FIG. 9, the elongate member 3 can also be scored along a longitudinal length of the elongate member, from one opposite end to the other opposite end, in a middle portion so as to break apart when a force is applied to the middle portion. As a result, the user can separate the menthol medicament for immediate use from the eucalyptus medicament for later use.

Figure 7:
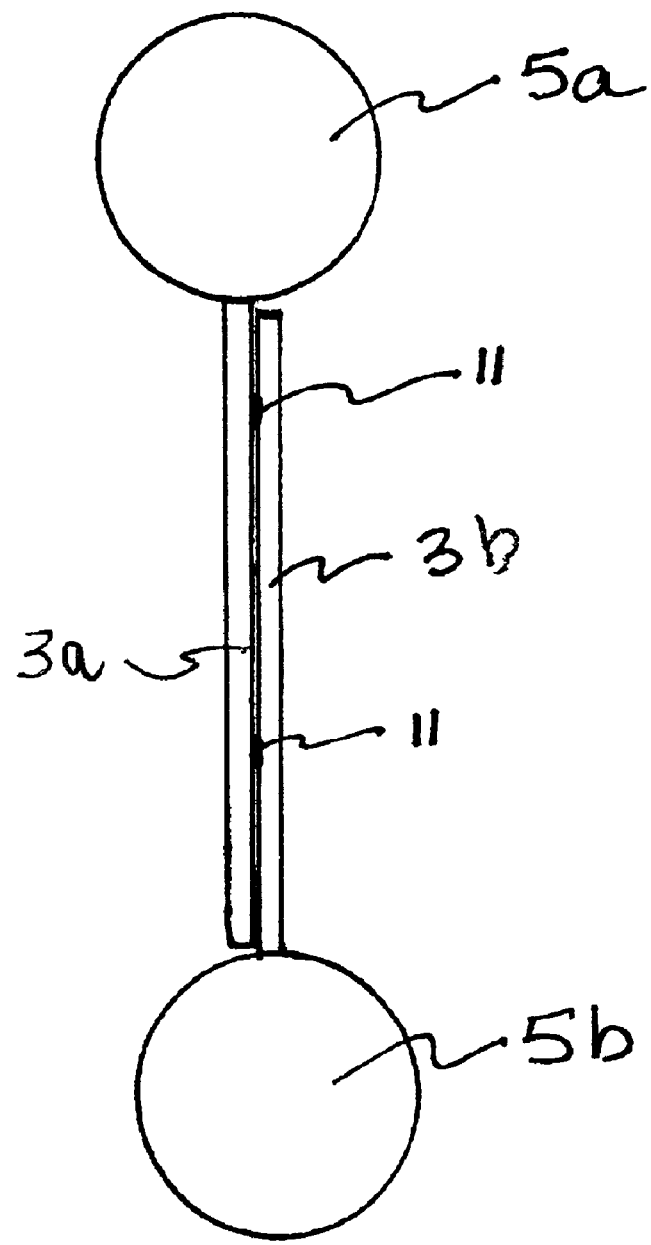
FIG. 7 is a view of the parallel elongate member portions of a third embodiment of the present invention.

In another embodiment shown in FIG. 7, the device 1 can have two elongate member portions 3a, 3b disposed in parallel to each other. One elongate member portion having a menthol medicament disposed at one end and the other elongate member portion having the eucalyptus medicament disposed at one end. An adhesive 11 along the longitudinal length of the elongate member portions can join the two elongate member portions. With this arrangement, the menthol medicament can be separated for immediate use, from the eucalyptus medicament, which can be used later.

The user can suppress a cough and provide cold relief by using the device in the following manner. First, the user must remove a wrapper disposed around the menthol medicament for sanitary purposes. Second, the user must insert the menthol medicament into the mouth, closing the mouth over the menthol medicament and placing the menthol medicament between the tongue and hard palate of the mouth. Third, the user must forcefully expel air from the lungs and tighten the stomach muscles, take deep breaths through the nose while closed-mouth coughing from the stomach. The user can then breathe normally through the nose.

The user can soothe their throat thereby providing cold relief by using the device in the following manner. After removing a wrapper disposed around each oral medicament for safety purposes, the user must first insert the eucalyptus medicament into the mouth. The eucalyptus medicament is disposed at an opposite end of the elongate member from the menthol medicament. Second, the user must insert the eucalyptus medicament into the mouth and close the mouth over the eucalyptus medicament, placing the eucalyptus medicament between the tongue and hard palate of the mouth. Third, the user must forcefully expel air from the lungs and tighten the stomach muscles, taking deep breaths while closed-mouth coughing from the stomach. The user must then breathe normally through the nose.

The present invention may be embodied in other specific forms without departing from the spirit or essential characteristics thereof. The presently disclosed embodiments are therefore to be considered in all respects as illustrative and not restrictive, the scope of the invention being indicated by the appended claims, rather than the foregoing description, and all changes which come within the meaning and range of equivalency of the claims are, therefore, to be embraced therein.

What is claimed is:

1. A double-headed, closed-mouth cough suppressant device comprising at least one elongate member, a first oral medicament and a second oral medicament, the at least one elongate member having opposite first and second ends wherein the first oral medicament is disposed at a first end and the second oral medicament is disposed at a second end, wherein the first oral medicament and second oral medicament are not the same medicament, thereby enabling the separate administration of the first oral medicament and the second oral medicament, the first end and the second end are permanently fixed together by said at least one elongate member, and the first oral medicament is menthol and the second oral medicament is eucalyptus.

2. The device according to claim 1, wherein the first and second oral medicaments are solid and have an aperture disposed therein and the opposite ends of the at least one elongate member are positioned within the aperture.

3. The device according to claim 1, wherein the first and second oral medicaments are flavored.

4. The device according to claim 1, wherein the at least one elongate member is a rigid member.

5. The device according to claim 4, wherein the at least one elongate member is a paper stick.

6. The device according to claim 4, wherein the at least one elongate member is plastic.

7. The device according to claim 1, wherein the first and second oral medicaments have curved perimeters.

8. The device according to claim 7, wherein the first and second oral medicaments are spherical.

9. The device according to claim 7, wherein the first and second oral medicaments are disk-shaped.

10. The device according to claim 1, wherein the first and second oral medicaments dissolve upon contact with a fluid.

11. The device according to claim 1, wherein the at least one elongate member is scored along the longitudinal length in a middle portion thereof so as to break apart when a force is applied to the middle portion.

12. A double-headed, closed-mouth cough suppressant and cold relief device comprising:

at least two oral medicaments;

a first elongate member portion having a tapered end wherein one of the at least two oral medicaments disposed at an end opposite to the tapered end;

a second elongate member portion being hollow and larger in diameter than the first elongate member portion, the second elongate member portion having a tapered first end on which another of the at least two oral medicaments is disposed and a second end;

wherein the tapered end of the first elongate member portion is permanently fixed to the second end of the second elongate member portion, the first elongate member portion being disposed within the second elongate member portion, and the first oral medicament is menthol and the second oral medicament is eucalyptus.

13. The device according to claim 12, wherein the first and second elongate member portions are readily separated when the first and the second elongate member portions are pulled in opposite directions.

14. A double-headed, closed-mouth cough suppressant device comprising at least one elongate member, a first oral medicament and a second oral medicament, the at least one elongate member having a first end and an opposite second end wherein the first oral medicament is disposed at a first end and the second oral medicament is disposed at an opposite second end, and wherein the at least one elongate member comprises two parallel elongate member portions, an adhesive joins the parallel elongate member portions along a longitudinal side, and the first oral medicament is menthol and the second oral medicament is eucalyptus.

* * * * *